(12) United States Patent
Jo et al.

(10) Patent No.: US 10,952,946 B1
(45) Date of Patent: Mar. 23, 2021

(54) SELF-OXIDATIVE HAIR DYE COMPOSITION AND DYEING METHOD USING SAME

(71) Applicant: Dong Sung Pharm. Co., Ltd., Seoul (KR)

(72) Inventors: Bonglim Jo, Gyeonggi-do (KR); Hyejin Moon, Gyeonggi-do (KR); Juhee Hong, Seoul (KR); Yuna Sim, Seoul (KR)

(73) Assignee: Dong Sung Pharm. Co., Ltd., Seoul (KR)

( * ) Notice: Subject to any disclaimer, the term of this patent is extended or adjusted under 35 U.S.C. 154(b) by 0 days.

(21) Appl. No.: 16/677,822

(22) Filed: Nov. 8, 2019

(51) Int. Cl.
*A61Q 5/10* (2006.01)
*A61K 8/41* (2006.01)
*A61K 8/34* (2006.01)
*A61K 8/368* (2006.01)

(52) U.S. Cl.
CPC .............. *A61K 8/415* (2013.01); *A61K 8/347* (2013.01); *A61K 8/368* (2013.01); *A61K 8/416* (2013.01); *A61Q 5/10* (2013.01); *A61K 2800/30* (2013.01); *A61K 2800/4324* (2013.01); *A61K 2800/522* (2013.01)

(58) Field of Classification Search
CPC .......... A61Q 5/10; A61K 8/415; A61K 8/347; A61K 8/416; A61K 2800/522; A61K 831/047; A61K 31/05
USPC ..................... 8/405, 406, 412, 424
See application file for complete search history.

(56) References Cited

U.S. PATENT DOCUMENTS

2005/0000035 A1* 1/2005 Chan .................. A61K 8/22
8/405

FOREIGN PATENT DOCUMENTS

JP H06192053 A * 7/1994 ............... A61Q 5/10

OTHER PUBLICATIONS

English Translation of the JP Patent No. JP-H06192053 A dated Aug. 10, 2020.*

* cited by examiner

*Primary Examiner* — Eisa B Elhilo
(74) *Attorney, Agent, or Firm* — Locke Lord LLP; Scott D. Wofsy

(57) ABSTRACT

Disclosed is a convenient single-agent-type self-oxidative hair dye that has the same effect as a conventional hair dye, which is used by mixing a hair dye as a first agent with an oxidizing agent as a second agent, by incorporating a dye having a benzenetriol structure as a self-oxidative dye that strongly absorbs oxygen in the air to cause oxidation in order to solve the problem of defective or insufficient dyeing occurring due to shortage of oxygen required for polymerization when dyeing hair using only the hair dye as the first agent without an oxidizing agent.

15 Claims, 5 Drawing Sheets
(4 of 5 Drawing Sheet(s) Filed in Color)

US 10,952,946 B1

SELF-OXIDATIVE HAIR DYE COMPOSITION AND DYEING METHOD USING SAME

BACKGROUND

(a) Technical Field

The present invention relates to a single-agent-type self-oxidative hair dye composition capable of dyeing hair using oxygen in the air without a separate oxidizing agent as a second agent and a dyeing method using the same.

(b) Background Art

Based on the degree of fastness of a dye on hair, hair dye products may be classified into three types, namely temporary hair dye products, semi-permanent hair dye products and permanent hair dye products.

A conventional oxidative permanent hair dye product includes, as a first agent, a hair dye including an oxidative dye and, as a second agent, an oxidizing agent including a hydrogen peroxide solution, is also called "oxidative permanent hair dye product" and has been the most widely used due to its excellent long-lasting color compared to conventional hair dye products.

Oxidative permanent hair dye, involving the use of a combination of the first agent with the second agent, is based on the dyeing principle whereby dye intermediates that do not have color, contained in the first agent, are polymerized with one another through oxidative reaction by oxygen molecules produced in the hydrogen peroxide solution of the second agent, ultimately resulting in coloring. The dyeing effect is increased as the reaction time between the first agent and the second agent becomes long after mixing.

However, when the first and second agents are not homogeneously mixed, oxygen of the hydrogen peroxide solution is produced only in a part of the mixture, but hydrogen peroxide solution is not present in the remaining part, so that oxygen is not produced there. In this case, when a heterogeneous mixture of the hair dye as the first agent and the oxidizing agent as the second agent is applied to the hair, one part of the hair is dyed to a normal color and the other part is not dyed or is non-uniformly dyed, for example, is dyed to a lighter or darker color than that intended, thus resulting in non-uniform and low-quality dyeing. In addition, it is very troublesome for an operator to mix the hair dye as the first agent with the oxidizing agent as the second agent.

Thus, there is increasing demand for novel hair dye compositions capable of dyeing hair with a single formulation, without a separate oxidizing agent, as a second agent.

The above information disclosed in this Background section is provided only for enhancement of understanding of the Background of the invention and therefore it may contain information that does not form the prior art that is already known in this country to a person of ordinary skill in the art.

SUMMARY OF THE DISCLOSURE

The present invention has been made in an effort to solve the above-described problems associated with the prior art.

It is one object of the present invention to provide a hair dye product which has a formulation of an oxidative permanent hair dye and is capable of dyeing hair using only a hair dye as a first agent without the necessity of mixing the hair dye as the first agent with an oxidizing agent as a second agent.

It is another object of the present invention to provide a convenient single-agent-type self-oxidative hair dye that has the same effect as a conventional hair dye, which is used by mixing a hair dye as a first agent with an oxidizing agent as a second agent, by incorporating a dye having a benzenetriol structure as a self-oxidative dye that strongly absorbs oxygen in the air to cause oxidation in order to solve the problem of defective or insufficient dyeing occurring due to shortage of oxygen required for polymerization when dyeing hair using only the hair dye as the first agent without an oxidizing agent.

In addition, the benzenetriol compound, which is a self-oxidative dye, is very unstable in an aqueous solution and thus is disadvantageous in that the hair dye effect disappears over time. This disadvantage remains unsolved.

Accordingly, it is another object of the present invention to devise a method for securing the stability of the benzenetriol compound in an aqueous solution and to provide an excellent single-agent-type self-oxidizing hair dye having stable hair-dyeing capability.

The objects of the present invention are not limited to those described above. The objects of the present invention will be clearly understood from the following description and can be implemented by the means defined in the claims and combinations thereof.

In one aspect, the present invention provides a self-oxidizing hair dye composition, wherein the composition includes a self-oxidative dye having a structure containing at least three oxidizable groups directly connected to a benzene ring, wherein the self-oxidative dye is present in an amount of 0.5 to 4.0% by weight with respect to the total weight of the composition.

The self-oxidative dye may include at least one of 1,2,4-trihydroxybenzene, 2,4-diaminophenol, pyrogallol and gallic acid.

The self-oxidative dye may have a structure having an oxidizable group at positions 1, 2 and 4 of a benzene ring.

The self-oxidative dye may include at least one of 1,2,4-trihydroxybenzene and 2,4-diaminophenol.

The self-oxidizing hair dye composition may further include an ammonium salt as an alkaline buffer.

The alkaline buffer may include at least one of ammonium bicarbonate, ammonium carbonate and ammonium chloride.

The alkaline buffer may be present in an amount of 0.5 to 6.0% by weight with respect to the total amount of the composition.

The composition may be not used in combination with an oxidizing agent containing a hydrogen peroxide solution.

The composition may include 3% or less by weight of an antioxidant with respect to the total amount of the composition.

The self-oxidative dye may include at least one of 1,2,4-trihydroxybenzene and 2,4-diaminophenol and the composition may include 0.5 to 4.0% by weight of the self-oxidative dye, 0.5 to 6.0% by weight of the alkaline buffer and 3% or less by weight of the antioxidant with respect to the total amount of the composition.

The composition may include 0.5 to 4.0% by weight of the self-oxidative dye, 0.5 to 6.0% by weight of the alkaline buffer, 0.1 to 1.0% by weight of the antioxidant and 0.1 to 8.0% by weight of the oxidative dye, with respect to the total amount of the composition.

In another aspect, the present invention provides a method of dyeing hair of a subject in need of hair dyeing including applying a self-oxidizing hair dye composition to the hair of the subject, wherein the self-oxidizing hair dye composition includes a self-oxidative dye having a structure containing at least three oxidizable groups directly connected to a benzene ring, wherein the self-oxidative dye is present in an amount of 0.5 to 4.0% by weight with respect to the total weight of the composition.

The self-oxidative dye may have a structure having an oxidizable group at positions 1, 2 and 4 of a benzene ring.

The self-oxidative dye may include at least one of 1,2,4-trihydroxybenzene and 2,4-diaminophenol.

The composition may further include 0.5 to 6.0% by weight of an ammonium salt as an alkaline buffer with respect to the total weight of the composition.

The self-oxidative dye may include at least one of 1,2,4-trihydroxybenzene and 2,4-diaminophenol, wherein the composition includes 0.5 to 4.0% by weight of the self-oxidative dye, 0.5 to 6.0% by weight of the alkaline buffer and 3% or less by weight of the antioxidant with respect to the total amount of the composition.

The applying the self-oxidizing hair dye composition to the hair of the subject may exclude mixing the self-oxidizing hair dye composition with an oxidizing agent containing a hydrogen peroxide solution.

In another aspect, the present invention provides a method of preparing the self-oxidizing hair dye composition.

Other aspects and preferred embodiments of the invention are discussed infra.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present invention will now be described in detail with reference to certain exemplary embodiments thereof, illustrated in the accompanying drawings, which are given hereinbelow by way of illustration only, and thus are not limitative of the present invention, and wherein.

DETAILED DESCRIPTION

Figure 1:
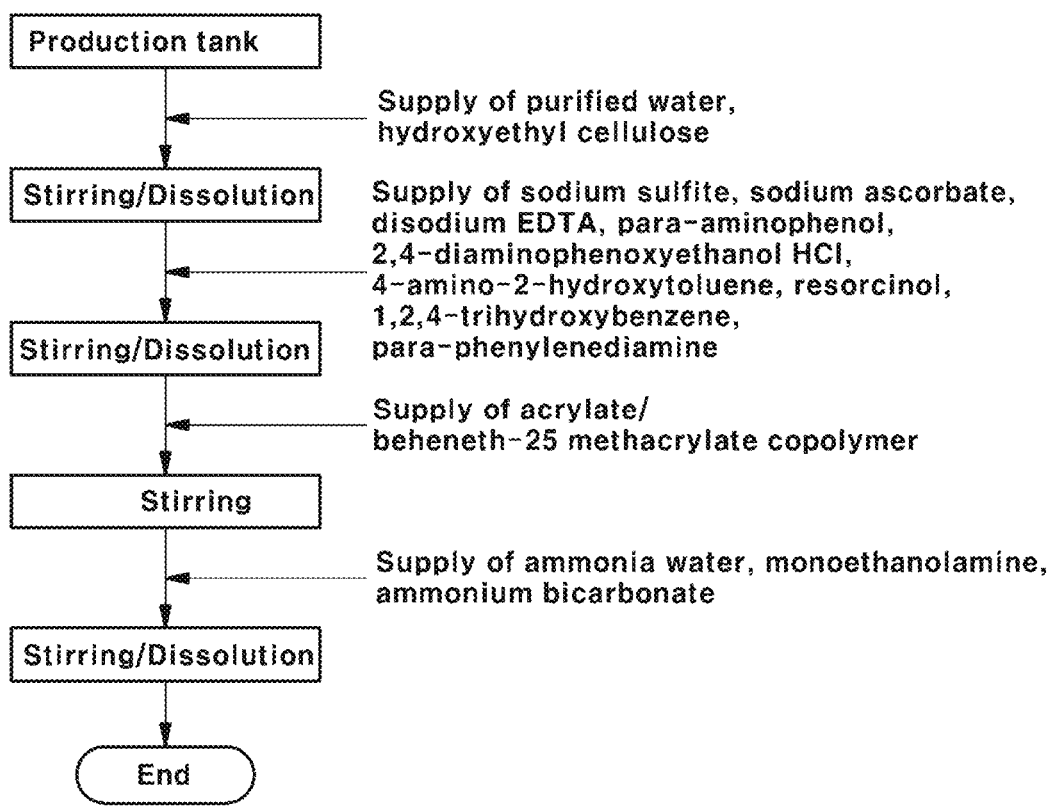
FIG. 1 is a schematic diagram illustrating a process of preparing hair dye compositions of Examples 1 to 2 of the present invention.
Figure 2A:
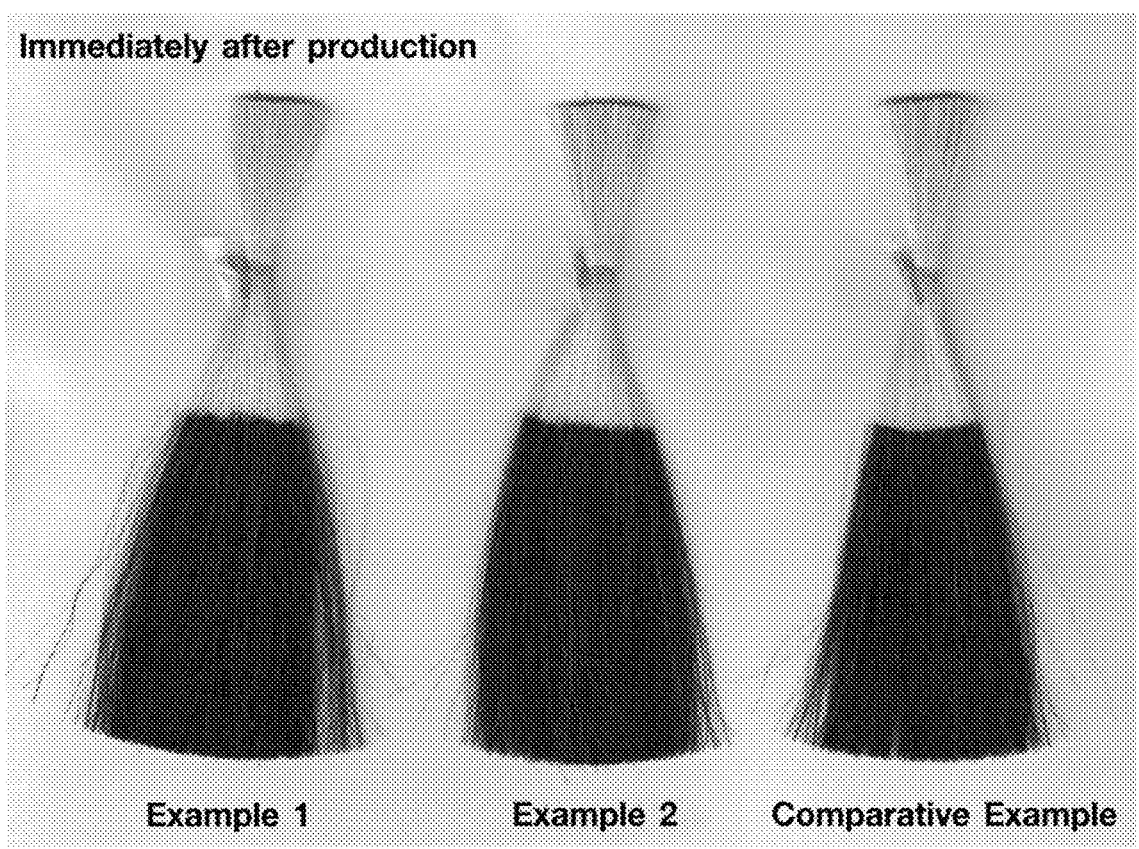
FIGS. 2A-2D shows the result of Experimental Example 1 according to the present invention.
Figure 2B:
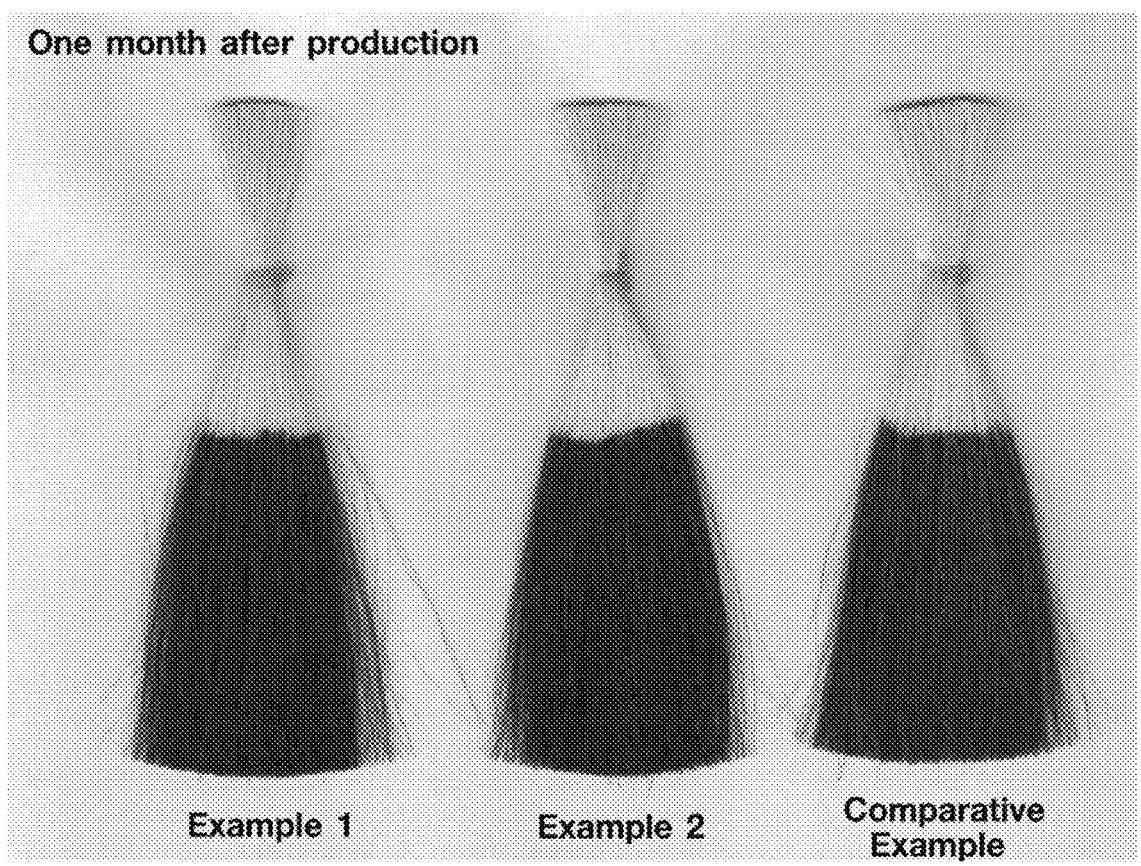
Figure 2C:
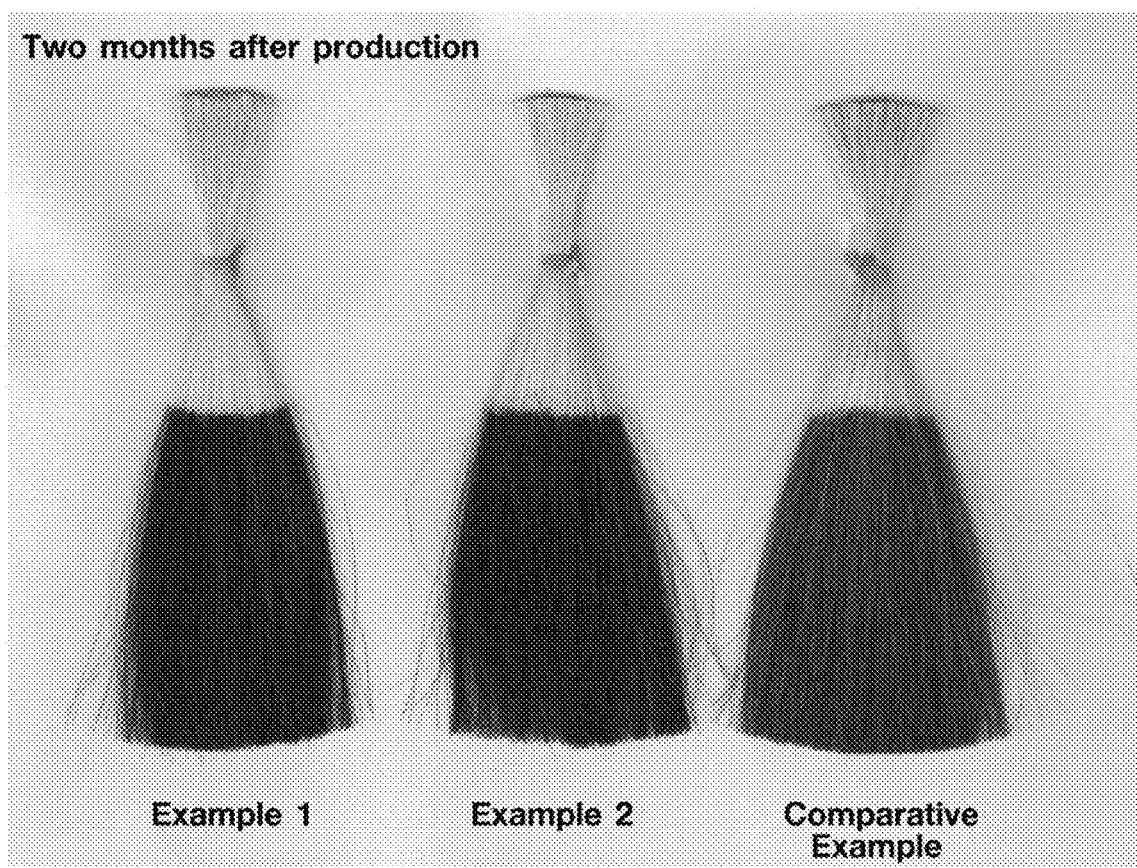
Figure 2D:
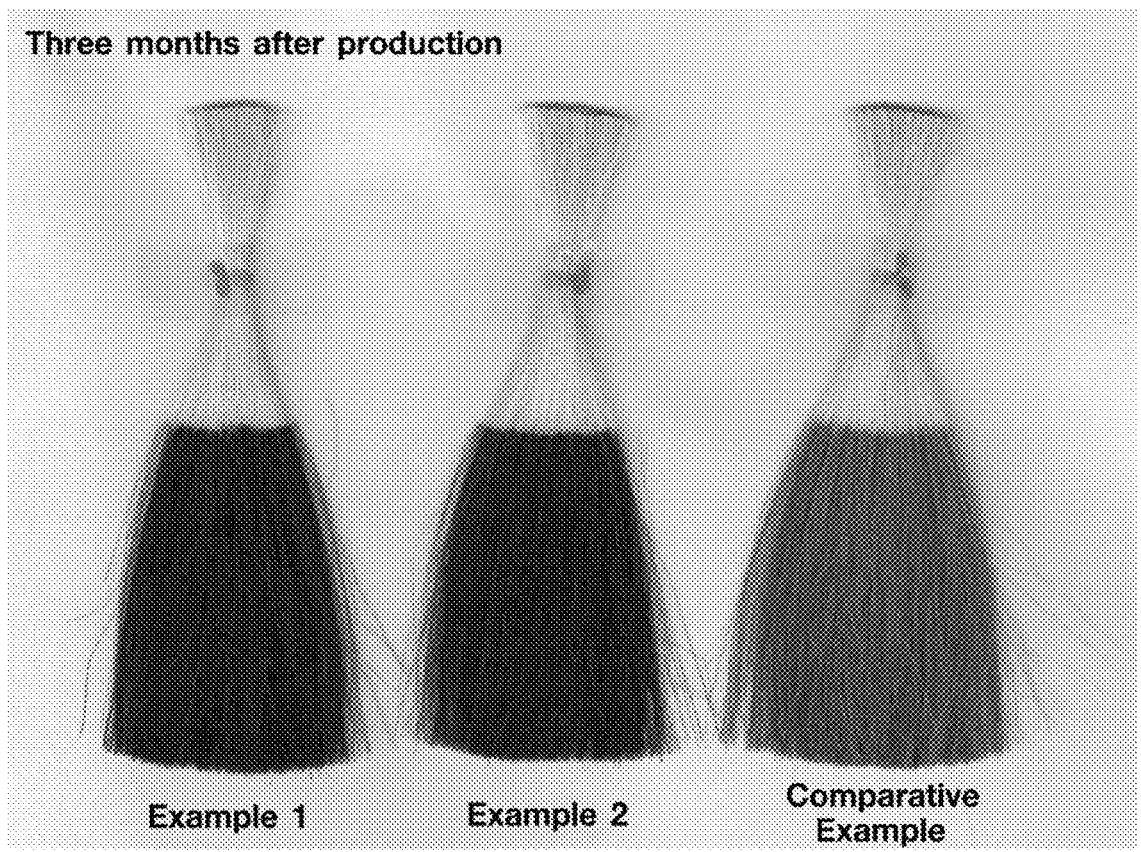

The objects described above, and other objects, features and advantages of the present invention, will be clearly understood from the following preferred embodiments with reference to the attached drawings. However, the present invention is not limited to the embodiments, and may be embodied in different forms. The embodiments are suggested only to offer a thorough and complete understanding of the disclosed context and to sufficiently inform those skilled in the art of the technical concept of the present invention.

Unless the context clearly indicates otherwise, all numbers, figures and/or expressions that represent ingredients, reaction conditions, polymer compositions and amounts of mixtures used in the specification are approximations that reflect various uncertainties of measurement occurring inherently in obtaining these figures, among other things. For this reason, it should be understood that, in all cases, the term "about" should be understood to modify all numbers, figures and/or expressions. In addition, when numerical ranges are disclosed in the description, these ranges are continuous and include all numbers from the minimum to the maximum including the maximum within each range unless otherwise defined. Furthermore, when the range refers to an integer, it includes all integers from the minimum to the maximum including the maximum within the range, unless otherwise defined.

It should be understood that, in the specification, when a range is referred to regarding a parameter, the parameter encompasses all figures including end points disclosed within the range. For example, the range of "5 to 10" includes figures of 5, 6, 7, 8, 9, and 10, as well as arbitrary sub-ranges, such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include numbers such as 10%, 11%, 12% and 13% as well as 30%, and any sub-ranges of 10% to 15%, 12% to 18%, or 20% to 30%, as well as any numbers, such as 10.5%, 15.5% and 25.5%, between appropriate integers that fall within the range.

Hereinafter, the present invention will be described in detail.

In order to achieve the objects of the present invention, the present invention provides a very convenient oxidative-type permanent hair dye composition that enables a conventional oxidative dye mixed therein to cause oxidative polymerization and thus realize dyeing without any oxidizing agent as a second agent by adding a specific proportion of a dye having a benzenetriol structure as a self-oxidative dye that strongly absorbs oxygen in the air and thus causes an oxidation reaction to a conventional hair dye using an oxidative dye.

In addition, conventional self-oxidative dyes having a benzenetriol structure are unstable in an aqueous solution and have a problem in which the color of hair dyed 2 to 6 months after the production thereof is about 10 to 50% poorer than that of hair dyed immediately after production, and the color almost disappears about one year.

Therefore, the present invention has been completed based on the finding that uniform dyeing is possible without any change in the result of hair dyeing over time when a specific buffer is added to the oxidative-type permanent hair dye as a first agent containing benzenetriol in order to solve the problem of very difficult commercialization of the conventional technology described above.

Therefore, the present invention is capable of dyeing hair with the same dyeing capability and the same color permanence as a conventional hair dye including a combination of a hair dye as a first agent and an oxidizing agent as a second agent by adding an alkaline buffer to an oxidative permanent hair dye including a conventional oxidative dye and a self-oxidative dye, namely benzenetriol.

In addition, the present invention provides a dye composition using a hydrophilic thickener, rather than using ionic surfactants and oily components such as fatty alcohols and fatty acids in order to facilitate the penetration of oxygen in the air.

The single-agent-type self-oxidizing permanent hair dye including a dye having a benzenetriol structure according to the present invention is capable of securing the stability of benzenetriol, which is unstable in an aqueous solution, and is capable of providing the same dyeing capability as a conventional two-agent-type permanent hair dye even with a hair dye as a first agent, by adding an alkaline buffer as a stabilizer thereto.

Among the compounds having the benzenetriol structure, compounds having an oxidizable group at positions 1, 2 and 4 of benzene are capable of rapidly causing an oxidation reaction by oxygen in the air. Benzene induces an oxidation reaction alone when an oxidizable element is added at positions 1, 2 and 4 based on the characteristics of the molecular structure.

Benzenetriol used in the present invention has three oxidizable groups added at positions 1, 2 and 4 of benzene and thus is rapidly oxidized with only a small amount of oxygen, compared to a compound having one oxidizable group added at each position. For this reason, such a compound is also referred to as "self-oxidative dye".

These self-oxidative dyes are highly reactive, but this also means that they are very unstable in an aqueous solution. Attempts to develop hair dyes dyed using only a hair dye as a first agent using a self-oxidative dye have been steadily made since the 1960s, but resultant hair dyes have not been developed as commercial products due to the lack of stability thereof.

In general, oxidative dyes have a very fast reaction rate when the pH is acidic and a relatively slow reaction rate when the pH is basic. The pH of conventional oxidative permanent hair dyes is basic, for example, about 9 to 11, so most oxidative dyes remain stable due to the presence of a certain content range of antioxidants before contacting oxygen, but dyes such as benzenetriol are unstable even under these conditions and lose the characteristics thereof over time.

In order to compensate for this problem, methods of increasing the amount of antioxidants or increasing the amount of self-oxidative dyes have been suggested. However, when the amount of antioxidants is increased, there is a problem in that the oxidation reaction of other conventional oxidation dyes included therein is inhibited, and thus the color is not properly represented. In addition, an increase in the amount of self-oxidative dye merely results in increased instability over time, and is not suitable as a fundamental alternative.

However, the prior art has failed to take into consideration the fact that conventional oxidation-type dyes are relatively stable at pH 9-10, but the solutions have different alkalinities, affecting the stability and dyeing capability of the dye, when the type and amount of alkaline agents are different even at the same pH.

Therefore, the present invention suggests a method of increasing the stability of the benzenetriol dye by adding an alkaline buffer to a single-agent-type self-oxidizing permanent hair dye.

The alkaline buffer is preferably an ammonium salt and may be ammonium bicarbonate, ammonium carbonate or ammonium chloride.

"Alkalinity" refers to the total amount of all alkali components present in an aqueous solution and is a concept different from pH. That is, high alkalinity does not necessarily mean high pH. Based on this principle, the fact that benzenetriol, which is a self-oxidative dye, is stably maintained when the alkalinity is increased by adding an alkaline buffer at pH 9 to 10, at which a common oxidative dye is stable, was first noted, and the present invention has been completed based on the finding.

The amount of the alkaline buffer that is used is 0.5 to 6.0% by weight with respect to the total weight of the hair dye composition. When the amount of the alkaline buffer exceeds 6.0% by weight, it may precipitate, depending on the formulation of the hair dye. Thus, the amount of the used alkaline buffer is preferably within the range above.

The single-agent-type self-oxidizing permanent hair dye according to the present invention may utilize the components used in conventional oxidative permanent hair dyes.

In one embodiment, the single-agent-type self-oxidizing permanent hair dye composition according to the present invention may include a hydrophilic thickener, an oxidative dye, a self-oxidative dye, an antioxidant, a metal-blocking agent, an alkaline agent and purified water, in addition to the alkaline buffer.

The specific content of each component is 0.5 to 6.0% by weight of the alkaline buffer, 2.0 to 20.0% by weight of the hydrophilic thickener, 0.1 to 1.0% by weight of the antioxidant, 0.1 to 8.0% by weight of the oxidative dye, 0.5 to 4.0% by weight of the self-oxidative dye, 0.05 to 0.4% by weight of the metal-blocking agent, 1.0 to 15.0% by weight of the alkaline agent and 54.40 to 95.75% by weight of the purified water.

The hydrophilic thickener may be a cellulose-based thickener, a polyacrylic acid polymer or the like, and in particular, may be hydroxyethyl cellulose, xanthan gum, cellulose gum (sodium CMC), a carbomer, an acrylate/beheneth-25 methacrylate copolymer, an acrylate/C10-30 alkyl acrylate crosspolymer or the like.

The oxidative dye may be one used in a conventional oxidized permanent hair dye. Specifically, examples of preferred oxidative dyes include p-phenylenediamine and sulfates thereof or hydrochlorides thereof, toluene-2,5-diamine and sulfates thereof or hydrochlorides thereof, o-aminophenol and sulfates thereof, m-aminophenol and sulfates thereof or hydrochlorides thereof, p-aminophenol and sulfates thereof or hydrochlorides thereof, m-phenylenediamine and sulfates thereof or hydrochlorides thereof, resorcinol, 4-amino-2-hydroxytoluene, 4-amino-2-hydroxytoluene, 1-naphthol, N,N'-bis(2-hydroxyethyl)-p-phenylenediamine and sulfates thereof, 2-amino-5-nitrophenol, phenyl methyl pyrazolone, 2,4-diaminophenoxyethanol and sulfates thereof or hydrochlorides thereof, 2-nitro-p-phenylenediamine and sulfates thereof or hydrochlorides thereof, picramic acid, 2,6-diaminopyridine and the like.

The self-oxidative dye may be one used in a conventional oxidative permanent hair dye having a benzenetriol structure having an oxidizing group at positions 1, 2 and 4 of benzene. Specific examples of the self-oxidative dye include 1,2,4-trihydroxybenzene, 2,4-diaminophenol, pyrogallol, gallic acid and the like.

The antioxidant may be sodium sulfite, sodium ascorbate, thioglycolic acid, ammonium thioglycolate, ascorbic acid, erythorbic acid and the like.

The metal-blocking agent may be disodium EDTA, tetrasodium EDTA or the like.

The alkaline agent may be ammonia water, monoethanolamine, triethanolamine, aminomethyl propanol or the like.

Hereinafter, various aspects of the present invention will be described.

In one aspect, the present invention is directed to a self-oxidizing hair dye composition, wherein the composition includes a self-oxidative dye having a structure containing at least three oxidizable groups directly connected to a benzene ring, wherein the self-oxidative dye is present in an amount of 0.5 to 4.0% by weight with respect to the total weight of the composition.

In an embodiment, the self-oxidative dye includes at least one of 1,2,4-trihydroxybenzene, 2,4-diaminophenol, pyrogallol and gallic acid.

In an embodiment, the self-oxidative dye has a structure having an oxidizable group at positions 1, 2 and 4 of a benzene ring.

In an embodiment, the self-oxidative dye includes at least one of 1,2,4-trihydroxybenzene and 2,4-diaminophenol.

In an embodiment, the composition further includes an ammonium salt as an alkaline buffer.

In an embodiment, the alkaline buffer includes at least one of ammonium bicarbonate, ammonium carbonate and ammonium chloride.

In an embodiment, the alkaline buffer is present in an amount of 0.5 to 6.0% by weight with respect to the total amount of the composition.

In an embodiment, the composition is not used in combination with an oxidizing agent containing a hydrogen peroxide solution.

In an embodiment, the composition includes 3% or less by weight of an antioxidant with respect to the total amount of the composition.

In an embodiment, the self-oxidative dye includes at least one of 1,2,4-trihydroxybenzene and 2,4-diaminophenol, and the composition includes 0.5 to 4.0% by weight of the self-oxidative dye, 0.5 to 6.0% by weight of the alkaline buffer and 3% or less by weight of the antioxidant with respect to the total amount of the composition.

In an embodiment, the composition includes 0.5 to 4.0% by weight of the self-oxidative dye, 0.5 to 6.0% by weight of the alkaline buffer, 0.1 to 1.0% by weight of the antioxidant and 0.1 to 8.0% by weight of the oxidative dye, with respect to the total amount of the composition.

In one aspect, the present invention is directed to a method of dyeing hair of a subject in need of hair dyeing, wherein the method includes applying a self-oxidizing hair dye composition to the hair of the subject, wherein the self-oxidizing hair dye composition includes a self-oxidative dye having a structure containing at least three oxidizable groups directly connected to a benzene ring, wherein the self-oxidative dye is present in an amount of 0.5 to 4.0% by weight with respect to the total weight of the composition.

In an embodiment, the self-oxidative dye has a structure having an oxidizable group at positions 1, 2 and 4 of a benzene ring.

In an embodiment, the self-oxidative dye has a structure having an oxidizable group at positions 1, 2 and 4 of a benzene ring.

In an embodiment, the self-oxidative dye includes at least one of 1,2,4-trihydroxybenzene and 2,4-diaminophenol.

In an embodiment, the composition further includes 0.5 to 6.0% by weight of an ammonium salt as an alkaline buffer with respect to the total weight of the composition.

In an embodiment, the self-oxidative dye includes at least one of 1,2,4-trihydroxybenzene and 2,4-diaminophenol, and the composition includes 0.5 to 4.0% by weight of the self-oxidative dye, 0.5 to 6.0% by weight of the alkaline buffer, and 3% or less by weight of the antioxidant with respect to the total amount of the composition.

In an embodiment, the applying the self-oxidizing hair dye composition to the hair of the subject excludes mixing the self-oxidizing hair dye composition with an oxidizing agent containing a hydrogen peroxide solution.

In another aspect, the present invention is directed to a method of preparing the self-oxidizing hair dye composition.

Hereinafter, the present invention will be described in more detail with reference to specific examples. However, the following examples are provided only for better understanding of the present invention, and should not be construed as limiting the scope of the present invention.

Example 1

In accordance with the process shown in FIG. 1, 2.0% by weight of ammonium bicarbonate as an alkaline buffer, 1.0% by weight of hydroxyethyl cellulose and 5.0% by weight of an acrylate/beheneth-25 methacrylate copolymer as hydrophilic thickeners, 2.0% by weight of para-phenylenediamine and 1.0% by weight of para-aminophenol as oxidative dyes, 0.5% by weight of 2,4-diaminophenoxyethanol HCl, 0.2% by weight of 4-amino-2-hydroxytoluene and 0.1% by weight of resorcinol as oxidizing dyes, 3.0% by weight of 1,2,4-trihydroxybenzene as a self-oxidizing dye, 0.2% by weight of sodium sulfite and 0.4% by weight of sodium ascorbate as antioxidants, 0.2% by weight of disodium EDTA as a metal-blocking agent, 4.0% by weight of aqueous ammonia and 2.0% by weight of monoethanolamine as alkalizing agents, and 77.5% by weight of purified water were added to a self-oxidative permanent hair dye composition, followed by stirring to prepare a self-oxidizing hair dye composition as a gel.

Example 2

A self-oxidizing hair dye composition was prepared in the same manner as in Example 1, except that the amount of ammonium bicarbonate in the composition was changed to 5.0% by weight and the amount of purified water therein was changed to 75.5% by weight.

Comparative Example

A self-oxidizing hair dye composition was prepared in the same manner as in Example 1, except that ammonium bicarbonate was not used and that the amount of purified water that was used was 79.5% by weight.

The contents of the hair dye compositions in Examples 1 to 2 and Comparative Example are summarized in Table 1 below.

TABLE 1

|  | Example 1 | Example 2 | Comparative Example |
|---|---|---|---|
| Ammonium bicarbonate | 2.00% | 5.00% | — |
| Hydroxyethyl cellulose | 1.00% | 1.00% | 1.00% |
| Acrylate/beheneth-25 methacrylate copolymer | 5.00% | 5.00% | 5.00% |
| Para-phenylenediamine | 2.00% | 2.00% | 2.00% |
| Para-aminophenol | 1.00% | 1.00% | 1.00% |
| 2,4-diam inophenoxyethanol HCl | 0.50% | 0.50% | 0.50% |
| 4-amino-2-hydroxytoluene | 0.20% | 0.20% | 0.20% |
| Resorcinol | 1.00% | 1.00% | 1.00% |
| 1,2,4-trihydroxybenzene | 3.00% | 3.00% | 3.00% |
| Sodium sulfite | 0.20% | 0.20% | 0.20% |
| Sodium ascorbate | 0.40% | 0.40% | 0.40% |
| Disodium EDTA | 0.20% | 0.20% | 0.20% |
| Aqueous ammonia | 4.00% | 4.00% | 4.00% |
| Monoethanolamine | 2.00% | 2.00% | 2.00% |
| Purified water | 77.50% | 75.50% | 79.50% |

Experimental Example 1: Evaluation of Hair Dyeing Capability According to Long-Term Storage The following experiment was conducted to evaluate the effect of the alkaline buffer on the long-term storage stability of the self-oxidizing hair dye composition.

In order to measure the dyeing capability of the hair dye compositions of Examples 1 to 2 and Comparative Example immediately after preparation and after storage at 40° C. for 30 days, 60 days and 90 days, the hair dye compositions prepared in Examples 1 to 2 and Comparative Example were applied to standard white hair having a weight of 1.0 g and a length of 8.0 cm and then left for 20 minutes, washed with running water using a shampoo solution for 2 minutes and dried to observe the hair dyeing capability.

Dyeing capability evaluation was performed using a colorimeter (model name; spectrophotometer CM-508C, manufacturer; MINOLTA CO. LTD., JAPAN) to determine the brightness value (L*) of each sample with reference to the standard white hair. The L* value indicates the brightness as a numerical value, which means that the larger the L* value, the brighter the color.

The result of hair dyeing test evaluation is shown in Table 2 below.

TABLE 2

|  | Example 1 | Example 2 | Comparative Example |
|---|---|---|---|
| Dyeing capability immediately after production (L*) | 18.04 | 18.69 | 18.28 |
| Dyeing capability after 30 days (L*) | 18.49 | 18.01 | 20.49 |
| Dyeing capability after 60 days (L*) | 18.14 | 18.52 | 24.91 |
| Dyeing capability after 90 days (L*) | 18.12 | 18.41 | 31.86 |

As can be seen in Table 2, Examples 1 and 2 showed no change in the dyed color, whether observed immediately after the production or after the lapse of time. However, in Comparative Example, the dyed hair had the same color as in Example immediately after production and remained relatively stable until one month after production in the case of observation over time, but became faded two months after the production.

In addition, the images of hairs dyed in Examples 1 and 2 and Comparative Example are shown in FIGS. 2A to 2D.

As is apparent from the foregoing, the self-oxidizing hair dye composition or the dyeing method using the same according to the present invention can provide convenience of direct application to hair without the inconvenience of the necessity of mixing the first agent corresponding to the hair dye with the second agent corresponding to the oxidizing agent.

The self-oxidizing hair dye composition or the dyeing method using the same according to the present invention does not use a second agent as an oxidizing agent, thus providing an effect of dyeing while preventing irritation of the scalp due to absence of the hydrogen peroxide solution.

The self-oxidizing hair dye composition according to the present invention can overcome the instability, that is, the self-oxidation of conventional self-oxidizing dyes, to thus maintain a stable state in the aqueous solution.

The self-oxidizing hair dye composition according to the present invention can be stored for a long time compared to the method of providing only a hair dye, as a first agent, without a conventional oxidizing agent due to maintenance of stability in an aqueous solution state.

The self-oxidizing hair dye composition according to the present invention provides the effect of avoiding the use of an excessive amount of antioxidants in order to solve the problem of stability associated with severe self-oxidation of the composition. In addition, problems in that the oxidation reaction of conventional oxidative dyes is inhibited and in that colors are not properly expressed can be solved, since it is not necessary to use excessive amounts of the antioxidants.

The self-oxidizing hair dye composition according to the present invention does not need to increase the amount of the self-oxidizing dye in order to solve the problem of stability of severe self-oxidation, thus being excellent economically.

The effects of the present invention are not limited to those mentioned above. It should be understood that the effects of the present invention include all effects that can be inferred from the description of the present invention.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A self-oxidizing hair dye composition,
    wherein the composition comprises a self-oxidative dye having a structure containing at least three oxidizable groups directly connected to a benzene ring and ammonium salt as an alkaline buffer, and
    wherein the self-oxidative dye is present in an amount of 0.5 to 4.0% by weight with respect to the total weight of the composition.

2. The self-oxidizing hair dye composition according to claim 1, wherein the self-oxidative dye comprises at least one of 1,2,4-trihydroxybenzene, 2,4-diaminophenol, pyrogallol and gallic acid.

3. The self-oxidizing hair dye composition according to claim 1, wherein the self-oxidative dye has a structure having an oxidizable group at positions 1, 2 and 4 of a benzene ring.

4. The self-oxidizing hair dye composition according to claim 3, wherein the self-oxidative dye comprises at least one of 1,2,4-trihydroxybenzene and 2,4-diaminophenol.

5. The self-oxidizing hair dye composition according to claim 1, wherein the alkaline buffer comprises at least one of ammonium bicarbonate, ammonium carbonate and ammonium chloride.

6. The self-oxidizing hair dye composition according to claim 1, wherein the alkaline buffer is present in an amount of 0.5 to 6.0% by weight with respect to the total amount of the composition.

7. The self-oxidizing hair dye composition according to claim 1, wherein the composition is not used in combination with an oxidizing agent containing a hydrogen peroxide solution.

8. The self-oxidizing hair dye composition according to claim 1, wherein the composition comprises 3% or less by weight of an antioxidant with respect to the total amount of the composition.

9. The self-oxidizing hair dye composition according to claim 1, wherein the self-oxidative dye comprises at least one of 1,2,4-trihydroxybenzene and 2,4-diaminophenol, and the composition comprises 0.5 to 4.0% by weight of the self-oxidative dye, 0.5 to 6.0% by weight of the alkaline buffer and 3% or less by weight of the antioxidant with respect to the total amount of the composition.

10. The self-oxidizing hair dye composition according to claim 9, wherein the composition comprises 0.1 to 1.0% by weight of the antioxidant with respect to the total amount of the composition.

11. A method of dyeing hair of a subject in need of hair dyeing comprising applying a self-oxidizing hair dye composition to the hair of the subject, wherein the self-oxidizing hair dye composition comprises a self-oxidative dye having a structure containing at least three oxidizable groups directly connected to a benzene ring and an ammonium salt as an alkaline buffer, wherein the self-oxidative dye is present in an amount of 0.5 to 4.0% by weight with respect to the total weight of the composition, and wherein the alkaline buffer is present in an amount of 0.5 to 6.0% by weight with respect to the total weight of the composition.

12. The method according to claim 11, wherein the self-oxidative dye has a structure having an oxidizable group at positions 1, 2 and 4 of a benzene ring.

13. The method according to claim 12, wherein the self-oxidative dye comprises at least one of 1,2,4-trihydroxybenzene and 2,4-diaminophenol.

14. The method according to claim 11, wherein the self-oxidative dye comprises at least one of 1,2,4-trihydroxybenzene and 2,4-diaminophenol, and wherein the composition comprises 0.5 to 4.0% by weight of the self-oxidative dye, 0.5 to 6.0% by weight of the alkaline buffer and 3% or less by weight of the antioxidant with respect to the total amount of the composition.

15. The method according to claim 11, wherein the applying the self-oxidizing hair dye composition to the hair of the subject excludes mixing the self-oxidizing hair dye composition with an oxidizing agent containing a hydrogen peroxide solution.

* * * * *